(12) United States Patent
Landau

(10) Patent No.: US 6,471,669 B2
(45) Date of Patent: Oct. 29, 2002

(54) DISPOSABLE NEEDLE-FREE INJECTION APPARATUS AND METHOD

(75) Inventor: Sergio Landau, Laguna Niguel, CA (US)

(73) Assignee: Bioject Medical Technologies Inc., Portland, OR (US)

( * ) Notice: Subject to any disclaimer, the term of this patent is extended or adjusted under 35 U.S.C. 154(b) by 29 days.

(21) Appl. No.: 09/799,787

(22) Filed: Mar. 5, 2001

(65) Prior Publication Data

US 2002/0123717 A1 Sep. 5, 2002

(51) Int. Cl.[7] .......................... A61M 5/30; A61M 37/00
(52) U.S. Cl. ......................... 604/68; 604/69; 604/143
(58) Field of Search ................. 604/68–72, 140, 604/141, 143, 148, 232, 131

(56) References Cited

U.S. PATENT DOCUMENTS

| | | | |
|---|---|---|---|
| 2,545,017 A | 3/1951 | Billingsley | 604/143 |
| 2,653,602 A | 9/1953 | Smoot | 604/68 |
| 2,667,874 A | 2/1954 | Dickinson, Jr. | 604/72 |
| 2,680,439 A | 6/1954 | Sutermeister | 604/70 |
| 3,110,309 A | 11/1963 | Higgins | 604/201 |
| 3,115,133 A | 12/1963 | Morando | 604/70 |
| 3,292,621 A | 12/1966 | Banker | 604/70 |
| 3,561,443 A | 2/1971 | Banker | 604/70 |
| 3,688,765 A | 9/1972 | Gasaway | 604/70 |
| 3,695,266 A | 10/1972 | Lussier | 604/70 |
| 3,714,943 A | 2/1973 | Yanof et al. | 604/70 |
| 3,853,125 A | 12/1974 | Clark et al. | 604/70 |
| 3,945,379 A | 3/1976 | Pritz et al. | 604/70 |
| 4,059,107 A | 11/1977 | Iriguchi et al. | 604/71 |
| 4,124,024 A | 11/1978 | Schwebel et al. | 604/69 |
| 4,596,556 A | 6/1986 | Morrow et al. | 604/70 |
| 4,680,027 A | 7/1987 | Parsons et al. | 604/68 |
| 4,717,384 A | 1/1988 | Waldiesen | 604/143 |
| 4,790,824 A | 12/1988 | Morrow et al. | 604/143 |
| 4,913,699 A | 4/1990 | Parsons | 604/68 |
| 4,940,460 A | 7/1990 | Casey et al. | 604/143 |
| 5,009,637 A | 4/1991 | Newman et al. | 604/68 |
| 5,024,656 A | 6/1991 | Gasaway | 604/70 |
| 5,383,851 A | 1/1995 | McKinnon, Jr. et al. | 604/68 |
| 5,503,627 A | 4/1996 | McKinnon et al. | 604/72 |
| 5,730,723 A | 3/1998 | Castellano et al. | 604/68 |
| 5,993,412 A | 11/1999 | Deily et al. | 604/68 |
| 6,096,002 A | 8/2000 | Landau | 604/68 |
| 6,132,395 A | 10/2000 | Landau et al. | 604/68 |
| 6,210,359 B1 | 4/2001 | Patel et al. | 604/68 |
| 6,224,567 B1 | 5/2001 | Roser | 604/68 |
| 6,264,629 B1 | 7/2001 | Landau | 604/68 |

FOREIGN PATENT DOCUMENTS

| | | |
|---|---|---|
| WO | WO00/33899 | 6/2000 |
| WO | WO00/48654 | 8/2000 |

*Primary Examiner*—Patrick Brinson
(74) *Attorney, Agent, or Firm*—Kolisch Hartwell, P.C.

(57) ABSTRACT

One form of the invention provides a needle-free injection system including the following components: a nozzle portion having a glass wall defining a drug storage space, and an injection wall defining a drug injection space, the injection wall being coaxial with the glass wall and defining a plurality of drug bypass conduits disposed adjacent a forward end of the drug injection space; an injection orifice defined at the forward end of the injection space; a drug plunger defining a rearward end of the storage space; a drug plug initially disposed between the storage space and the injection space, and being displaceable into the injection space adjacent the bypass conduits; and a pierceable gas cartridge for providing injection power to the drug plunger.

38 Claims, 8 Drawing Sheets

DISPOSABLE NEEDLE-FREE INJECTION APPARATUS AND METHOD

BACKGROUND OF THE INVENTION

The present invention relates generally to a single-use disposable needle-free (or needleless) jet injection device. Specifically, this invention relates to such a jet injection device that comprises a hand-held injector having a pre-filled drug cartridge sealingly carrying injectable drug, a sealed cylinder of pressurized gas, a piercing mechanism for penetrating the gas cylinder, and a trigger device for releasing the discharge mechanism. The device is smaller and has fewer parts than prior disposable systems, and can be easily assembled and filled using automated equipment.

RELATED TECHNOLOGY

Needle-free or needleless hypodermic jet injection devices have been in commercial use for over 40 years. A number of these devices have used pressurized gas to power a hypodermic jet injection. The related technology includes a number of teachings for gas-powered injection devices, including: U.S. Pat. No. 4,596,556, issued to J. Thomas Morrow, et al.; U.S. Pat. No. 4,913,699, issued to James S. Parsons, and U.S. Pat. No. 5,730,723, issued to Thomas P. Castellano, et al. WIPO publication WO 97/37705 also discloses a gas powered disposable needle-free hypodermic jet injector.

The Morrow, et al. '556 patent is believed to teach a reusable hypodermic jet injection device in which a housing receives a shell or cartridge having a bore leading to a discharge aperture. Within the bore is received both a plunger sealingly engaging the bore, and a pressurized gas cylinder that rests against the plunger. The injection device includes a ram having a penetrating tip confronting a penetrable wall section and seal of the gas cylinder, and a discharge mechanism for driving the ram through the penetrable wall section of the gas cylinder when a trigger device is released. Discharge of the pressurized gas from the cylinder drives the plunger to effect a jet injection, and also drives the seal of the gas cylinder to effect resetting of the discharge mechanism. The shell with its plunger and spent gas cylinder is discarded after an injection; a new shell, pre-filled with medication and with a new gas cylinder, is used for each injection.

The Parsons '699 patent is believed to teach a single-use jet injector that is discarded after one use. This injector is believed to have a body with a pair of gas chambers separated by a breakable valve. One of the gas chambers contains a pressurized gas, while the other chamber is sealingly bounded by a piston that drives a plunger. The plunger sealingly bounds a chamber into which a dose of medication is loaded by the user before the injection. This medication dose chamber leads to an injection orifice so that when the valve is broken, the piston and plunger are moved by pressurized gas communicated to the second chamber, and the plunger drives the medication forcefully out of the injection orifice to form an injection jet. After a single use, the device is discarded.

The Castellano '723 patent, which was issued in 1998 and which does not cite the earlier Parsons '699 patent, is believed to teach substantially the same subject matter as Parsons et al.

WIPO publication WO 97/37705 published pursuant to a Patent Cooperation Treaty (PCT) application for joint inventors Terence Weston and Pixey Thomlea, is believed to disclose a disposable hypodermic jet injector in which the device is powered by a gas pressure spring of the type common in the tool and die art as a substitute for the conventional metal spring-powered ejector pin. In the Weston device, the ram of the gas pressure spring is held in a contracted position by a trigger mechanism. When the trigger mechanism is released, the gas pressure spring is supposed to expand and drive a piston sealingly received in a bore and leading to a fine-dimension orifice to produce a jet hypodermic injection from liquid held in the bore ahead of the piston.

The Weston device is thought to have several deficiencies such as difficult and costly manufacturing and sterilization processes because the pressurized gas and a drug dose need to be contained in the same package, and a possible inability to endure long-term storage while still retaining the gas pressure in the gas spring. In other words, the gas pressure spring of the Weston device contains only a small quantity of gas, and depends upon the sealing relationship of the ram of this spring with a cylinder within which the ram is movably and sealingly received in order to retain this gas pressure. Even a small amount of gas leakage over time will be enough to render this injector inoperative.

It also is known in this art to provide a needle-free injection system having two plungers that are initially spaced adjacent either end of a glass drug storage sleeve, with liquid drug being disposed between the plungers within the sleeve. Such a system also includes a plastic drug storage chamber disposed coaxially with and forwardly of the glass drug storage sleeve. The forward end of the plastic drug chamber terminates in an injection orifice. The plastic drug chamber includes an enlarged portion that permits drug to flow past the forward plunger when that plunger is aligned with the enlarged portion.

In this earlier system, axial force is exerted on the rear plunger immediately prior to injection. Because liquid drug is disposed in the space between the plungers, the plungers move in unison in a forward direction until the forward plunger is aligned with the enlarged portion. At that point, the continued forward travel of the rearward plunger forces liquid drug around the forward plunger until all of the drug is disposed in the plastic drug chamber forward of both plungers, which are now in abutment. The unit thus is ready for actuation.

When the unit is actuated the plungers both exert a forward axial force, causing liquid drug to be directed out of the injection orifice and into the patient.

SUMMARY OF THE INVENTION

One form of the invention provides a needle-free injection system including the following components: a nozzle portion having a glass wall defining a drug storage space, and an injection wall defining a drug injection space, the injection wall being coaxial with the glass wall and defining a plurality of drug bypass conduits disposed adjacent a forward end of the drug injection space; a body portion mounted to the nozzle portion such that relative axial movement may be effected between the portions; an injection orifice defined at the forward end of the injection space; a drug plunger defining a rearward end of the storage space; a drug plug initially disposed between the storage space and the injection space, and being displaceable into the injection space adjacent the bypass conduits; and a pierceable gas cartridge for providing injection power to the drug plunger.

Another form the invention takes is a needle-free injection system including the following components: a nozzle portion defining a forwardly-facing injection orifice; a body portion mounted to the nozzle portion, the portions being displaceable toward each other to prepare the system for actuation; and a safety tab for preventing actuation prior to the time that relative displacement is effected between the nozzle portion and the body portion, the safety tab being fragibly mounted to one of the body portion or the nozzle portion and including a contact part, the safety tab to be contacted and broken when the portions are displaced toward each other.

Yet another form the invention takes is a method for preparing a needle-free injection unit for injection, comprising the following steps: providing a storage compartment for liquid drug; positioning an injection orifice forwardly of the storage compartment, through which the liquid drug is selectively injected into the patient; providing a pressurized, pierceable gas storage cartridge with a system for conveying pressure to the storage compartment when the cartridge is pierced; positioning a seal between the cartridge and the storage compartment to prevent gas pressure from reaching the storage compartment after the cartridge is pierced, but prior to actuation of the unit, the seal being positioned such that the piercing of the cartridge provides axial pressure on the seal; providing a trigger having a roller positioned such that when axial pressure is provided on the trigger, an outward force is exerted on the trigger; and positioning a trigger actuator outwardly of the trigger to prevent the trigger from moving outwardly until the unit is actuated.

DETAILED DESCRIPTION OF PREFERRED EMBODIMENTS

Figure 1:
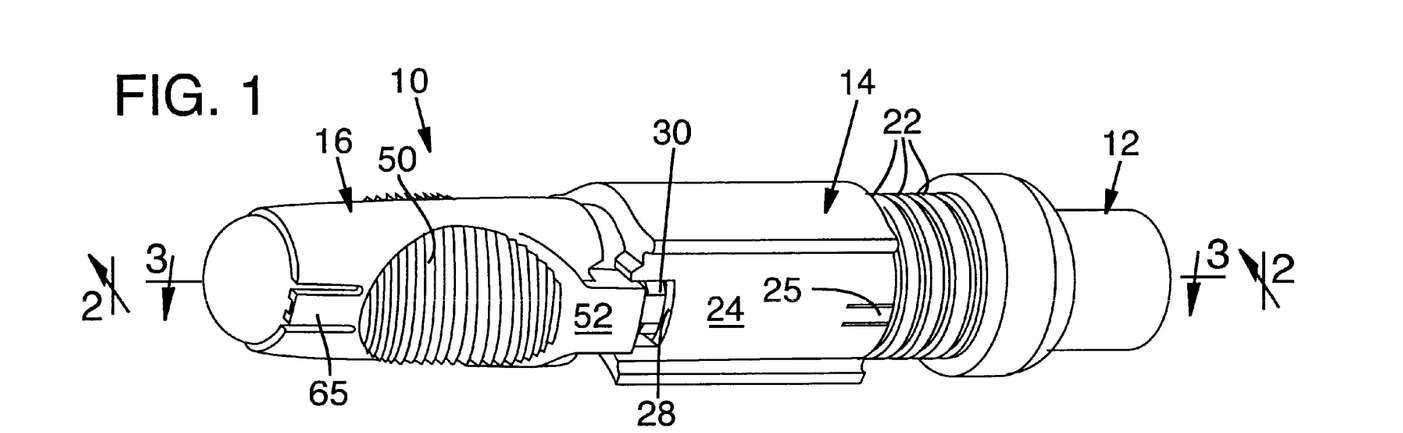
FIG. 1 is an isometric view of a first embodiment of the present invention, showing the unit ready for shipping to the patient.

The objects of the invention are best achieved when the invention takes the form of the embodiment depicted in the figures. FIGS. 1–11 depict a first embodiment of the apparatus that is designated generally with the numeral 10. FIG. 1 depicts the three basic components of the preferred embodiment 10—a nozzle portion 12, a body portion 14 and a trigger portion 16. These portions will be individually discussed as this description continues.

Figure 2:
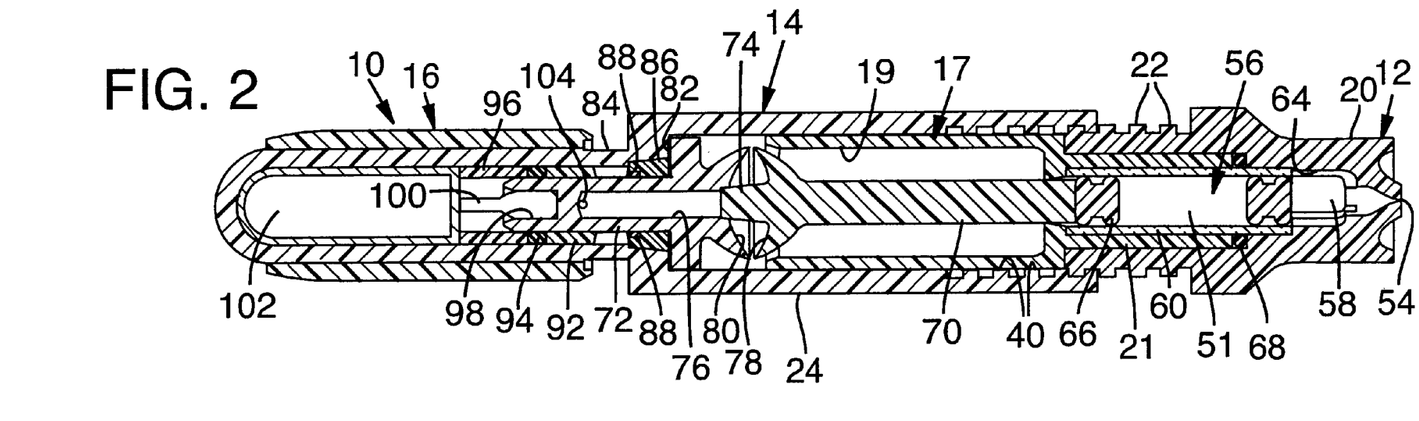
FIG. 2 is a side elevation sectional view taken along line 2—2 of FIG. 1.
Figure 3:
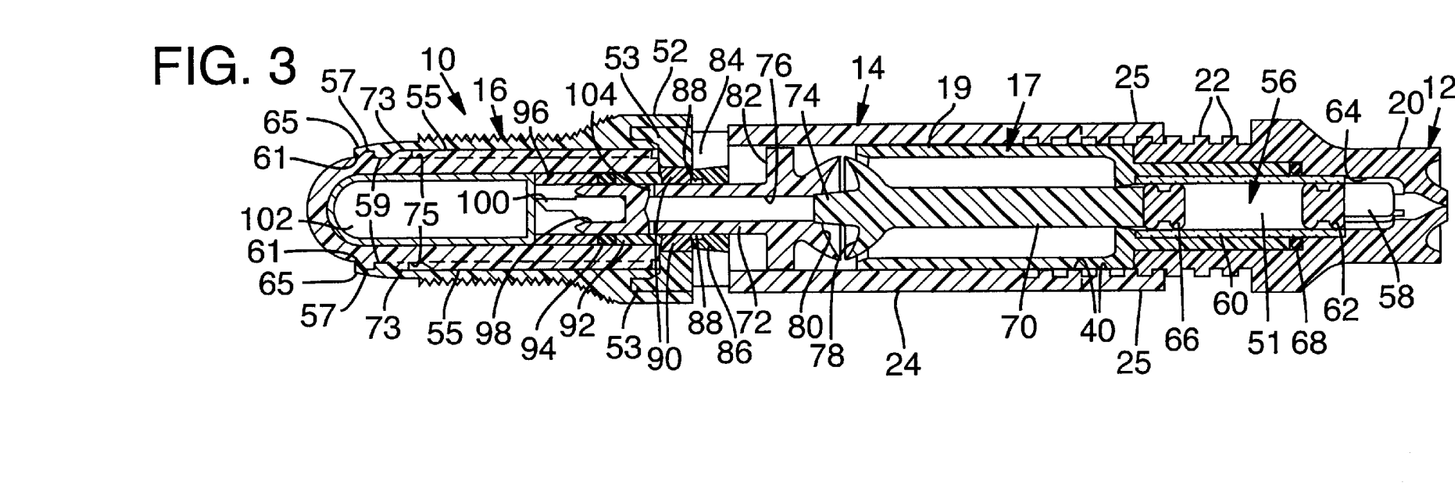
FIG. 3 is a side elevation sectional view taken along line 3—3 of FIG. 1, at 90° from the view of FIG. 2.

Reference should first be made to FIGS. 2 and 3, which depict apparatus 10 as it is packaged, shipped and received by the customer. The customer in this case may be a clinic, a physician or even a patient. Nozzle portion 12 includes outwardly facing threads 22 that are received in body portion 14, as will be explained in a moment. Extending between nozzle portion 12 and body portion 14 is an inner sleeve 17 having an enlarged section 19 disposed in the body portion and a reduced section 21 disposed in the nozzle portion. Sleeve 17 is sized to fit tightly into the nozzle portion. It is fit into the body portion in a tight sliding fit to permit the nozzle portion to be rotated into the body portion.

Body portion 14 includes a body 24 with a pair of nozzle portion engagement clips 25 designed to engage the nozzle portion. As shown best in FIG. 8A, each of the clips has an inwardly extending engagement nib 27. The engagement nibs 27 engage the proximal-most threads 22 to hold the body and nozzle portion together prior to the point that they are fully threaded into each other.

Figures 8, 8A:
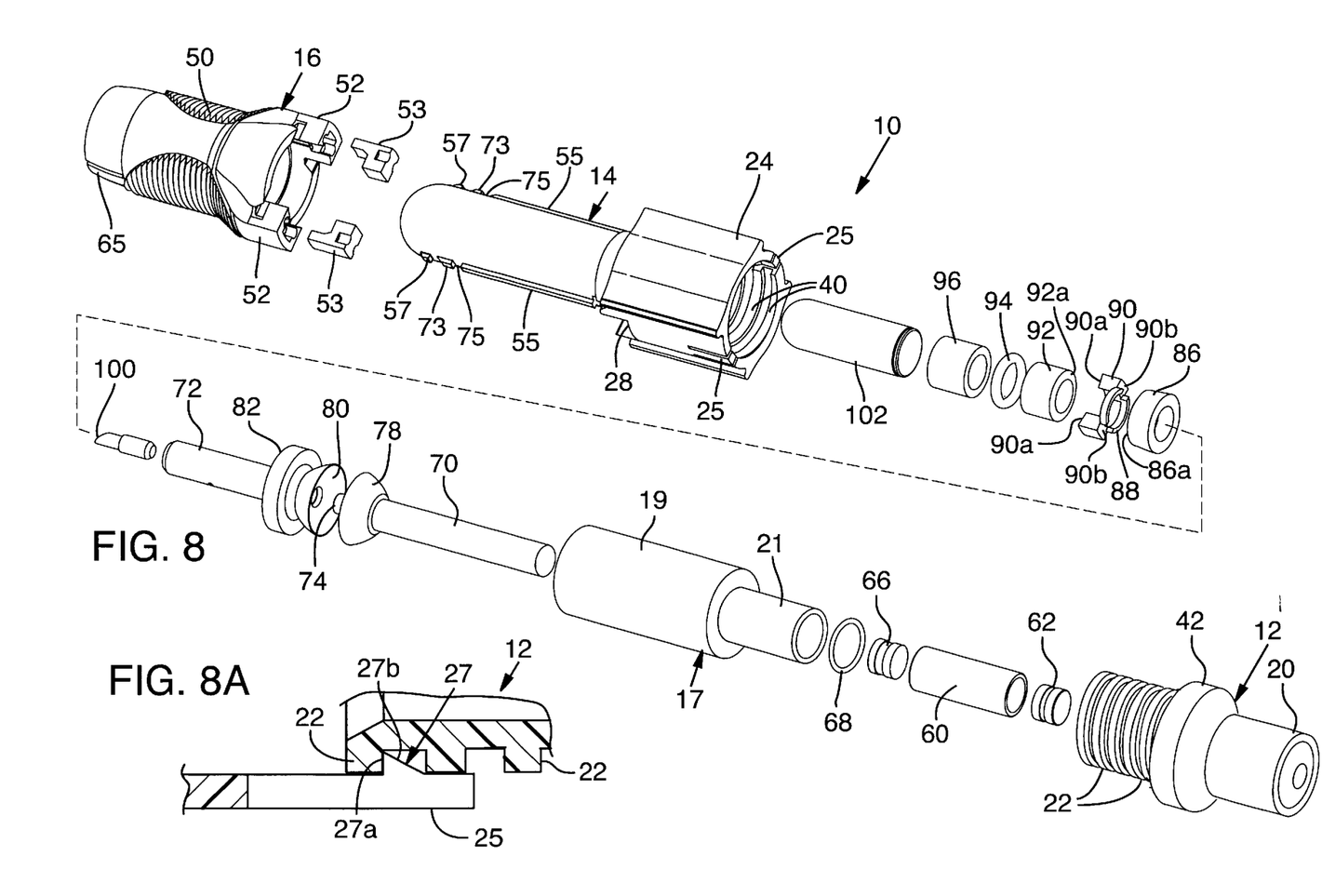
FIG. 8 is an exploded view of the embodiment of FIGS. 1–7.
FIG. 8A is an enlarged, schematic, fragmentary side elevation sectional view showing the leg and nib construction of the embodiment of FIGS. 1–8 that provides a capability of holding the nozzle portion in engagement with the body portion during storage and shipping.
Figure 9:
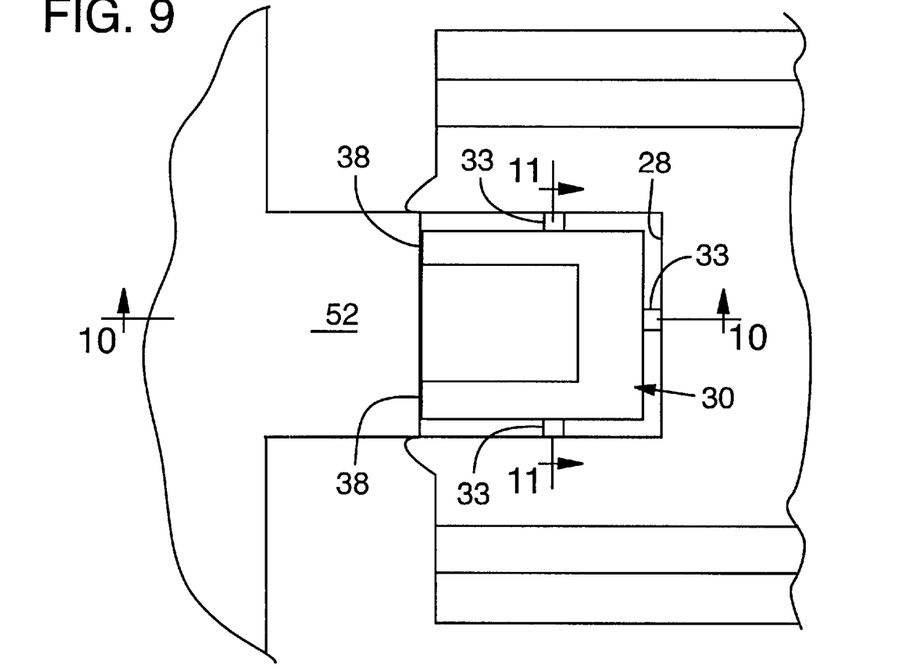
FIG. 9 is a schematic, fragmentary plan view of one of the safety tabs included in the embodiment of FIGS. 1–8.
Figure 10:
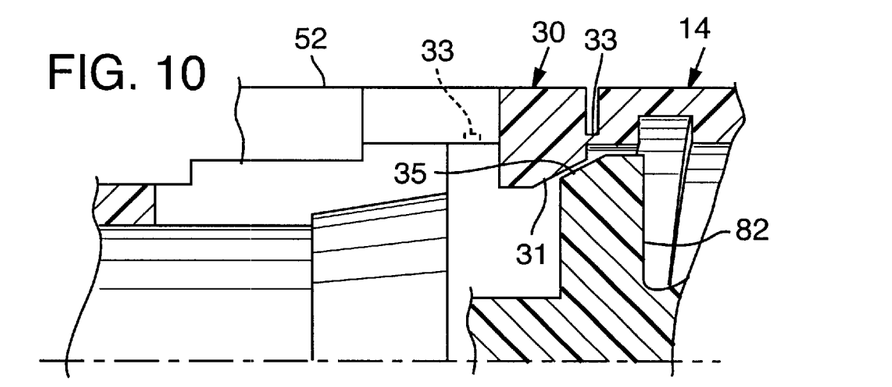
FIG. 10 is a side elevation sectional view taken along line 10—10 of FIG. 9.
Figure 11:
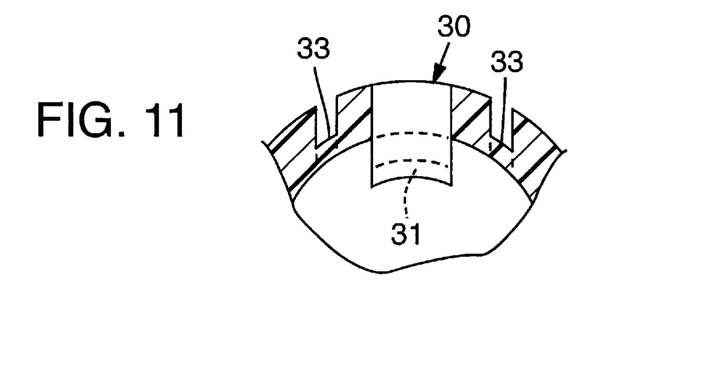
FIG. 11 is a fragmentary, end elevation sectional view taken along line 11—11 of FIG. 9.

More specifically, the embodiment shown in FIG. 8A has nibs 27, each of which include two faces. The proximal face 27a extends at about a 90° angle, while the distal face 27b extends at about a 45° angle. When first thread 22 is slid over the two clips 25 on the opposite sides of the body portion, the resiliency of the clips permits the clips to bend outwardly to receive the end of the nozzle portion. During this bending and insertion process, the 90° leading edge of the first thread 22 slides over the distal face 27b of nib 27. Clip 25 snaps back once the first thread has cleared the nib. The 90° nib face 27a complements the 90° leading edge of the first thread 22 to prevent the nozzle portion from falling out of or being removed from the body portion.

The resiliency of the two clips 25 provides resistance to the nozzle portion being pushed over the 45° face 27b of nib 27. Thus, during shipment the nozzle portion won't be sliding in and out of the body portion. Once the patient has received the apparatus 10 and wants to prepare it for actuation, he/she can thread the nozzle portion into the body portion, permitting the 90° face of the next thread 22 to ride over the 45° face 27b as clip 25 bends outwardly and snaps back into place once the second thread has cleared the 45° face 27b of nib 27.

Also included in body 24 is a pair of trigger engagement slots 28 that extend into the end of the body facing trigger portion 16 (see FIG. 1). Trigger engagement slots 28 are disposed 180° across the trigger portion from each other; only one of these slots shows in the figures.

FIGS. 1 and 9–11 depict a generally U-shaped safety tab 30 that is frangibly (or breakably) mounted by three thin webs 33 within one of the trigger engagement slots 28. Two of the safety tabs 30 may be provided, at the option of the designer, in which case, one safety tab 30 would be positioned within each of the trigger engagement slots 28. Safety tab 30 includes an inwardly-extending chamfered surface 31 (see FIG. 10) that is designed to be contacted by a corresponding chamfered surface to be described below.

Figure 4:
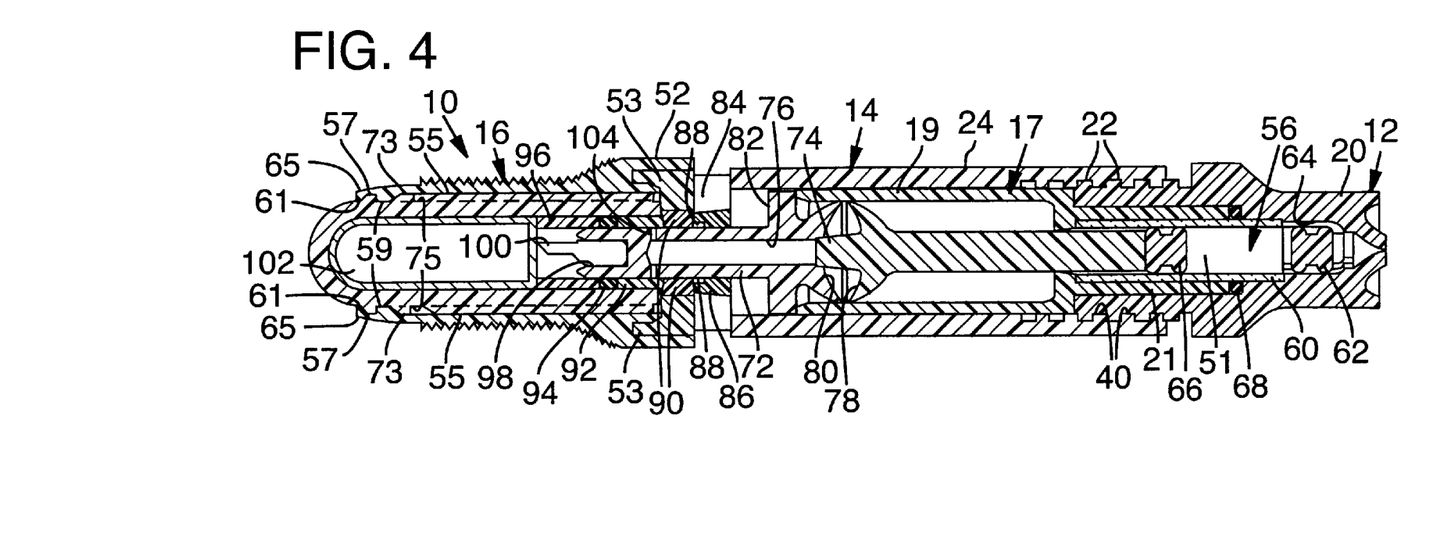
FIG. 4 is a side elevation sectional view corresponding to FIG. 3 except that the threaded nozzle portion is shown to be about half of the way threaded into the body portion, and the drug plunger and drug plug are shown shifted forwardly, with the drug plug seated in the forward end of the plastic drug chamber.
Figure 5:
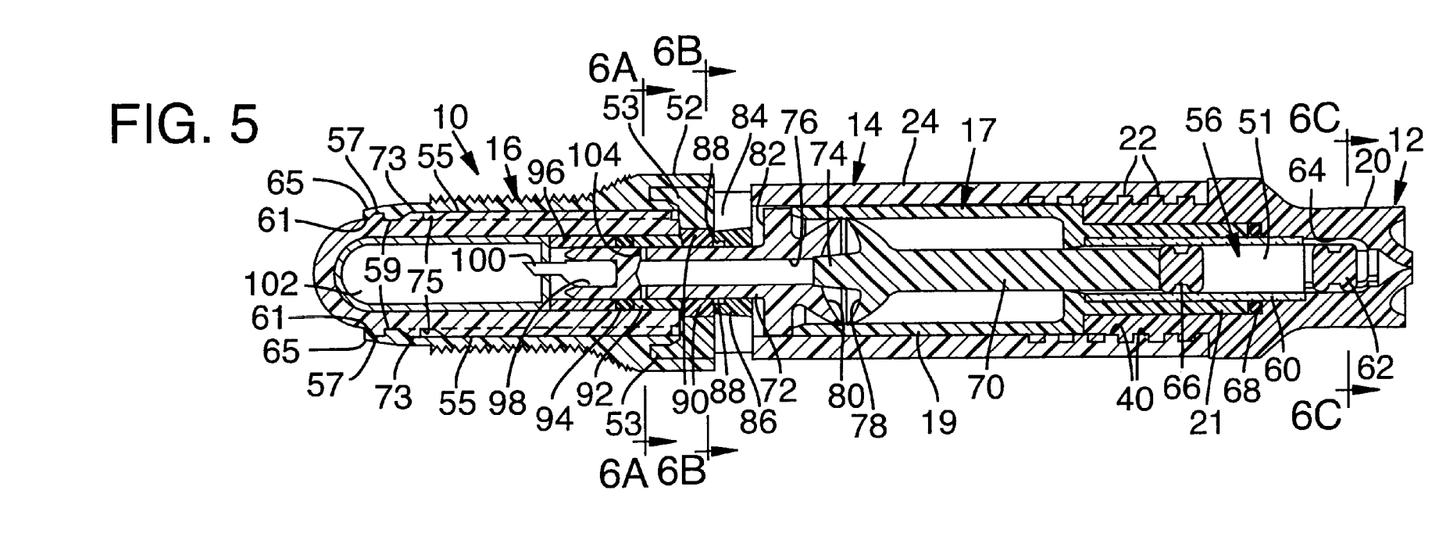
FIG. 5 is a view corresponding to FIG. 4 except that the gas cartridge is shown to be pierced as a result of the nozzle portion being turned entirely into the body portion; the apparatus is ready for injection.

As shown in FIGS. 2–8, threads 40 are included in the distal end of the inner side of body 24. These threads 40 complement threads 22 in nozzle portion 12, so that when the patient is ready to use apparatus 10 to effect injection, nozzle portion 12 may be rotated into body 24. FIG. 4 shows nozzle portion 12 to be threaded about halfway into body portion 14. By comparing FIGS. 3 and 4, it can be seen that a drug plunger 66 and a drug plug 62 (to be described below) have shifted to the right. With the components in this position the unit is considered primed because air has been removed from the front part of nozzle portion 12. FIG. 5 shows nozzle portion 12 to be threaded all of the way into body portion 14. In this final threading step a piercing pin 100 pierces a gas cartridge 102, and the apparatus is ready for injection. This operation of apparatus 10 will be explained in more detail below.

Again as shown best in FIGS. 1 and 2, trigger portion 16 includes a trigger actuation portion 50 that is in the form of two pads, one on each side of trigger portion 16. Trigger actuation portion 50 also includes a pair of axially extending trigger members 52 that are aligned with and extend slightly into trigger engagement slots 28 at 180° positions across the apparatus. Safety tab 30 is frangibly mounted in each trigger engagement slot 28 by thin webs 33 as mentioned above.

Referring now to FIG. 8, a pair of trigger actuators 53 are shown to be positioned within trigger members 52. These trigger actuators cooperate to hold a pair of trigger elements 90 in a radially inward position to prevent actuation of the apparatus until the trigger portion 16 is slid forward toward body portion 14. This operation will be described in more detail below.

FIG. 8 also shows a pair of longitudinally extending ribs 55 that fit into complementing slots (not shown) in trigger portion 16. These ribs 55 also show in FIG. 6A. Immediately rearward of these ribs are a pair of nibs 57 (see FIGS. 3–5,7 and 8), each of which includes a rearward inclined face so that trigger portion 16 can be slid onto this rearward part of the body.

As identified in FIGS. 3–5, a pair of corresponding trigger nibs 59 and 61 define a trigger portion slot (not shown) designed to receive body nibs 57 on each side of the trigger portion. The trigger nibs 59 and 61 are positioned on the inner side of a pair of clips 65 that are cut into the rear of trigger actuation portion 50. One of these clips 65 appears in FIGS. 1 and 8. Clips 65 are on opposite sides of the trigger portion, and provide the resiliency needed so that trigger portion 16 can snap into body portion 14. The complementing inclination of the nib faces permits the trigger actuation portion to slide forward during actuation, but does not permit the trigger portion to be removed from the body portion. It thus operates in much the same fashion as clip 25 discussed above.

FIG. 2 and subsequent figures show the interior, working portions of apparatus 10. Starting from the right in FIG. 2, an injection orifice 54 provides the means by which liquid drug exits apparatus 10 in a defined, high-pressure stream directed into the patient. A liquid drug chamber is depicted generally at 56, and includes a plastic drug chamber 58 defined by the inwardly facing wall of nozzle portion 12, and a drug storage chamber 51 defined by a glass cartridge 60. Glass cartridge 60 retains the liquid drug during storage and shipment and prior to the point that apparatus 10 is converted to its primed mode with nozzle portion 12 being rotated into body portion 14 as described above.

Positioned between drug storage chamber 51 and plastic drug chamber 58 is a drug plug 62. Positioned at the rearward or proximal end of drug storage chamber 51, within glass cartridge 60, is a drug plunger 66. The resilient material of which drug plunger 66 and drug plug 62 are fabricated is sufficiently impermeable that liquid drug absorption is not a problem. The material is also inert so that there is no chemical or biological reaction to the drug. Butyl rubber has both of these features.

In apparatus 10, glass cartridge 60 is provided to store the liquid drug. Most conventional plastics are too permeable to allow long-term storage, so liquid drug is stored in glass cartridge 60 in drug storage chamber 51, and is injected from plastic drug chamber 58, which is the ideal function of each material.

Defined in the walls of plastic drug chamber 58, at the forward end therof, are three drug bypass conduits 64, evenly spaced around the periphery at 120° increments. These are shown in cross-section in FIG. 6C. While three drug bypass conduits 64 are included, any number of conduits can be utilized. However many conduits are included, they should be symmetrically positioned around the periphery of plastic drug chamber 58.

As shown best in FIGS. 2 and 3, bypass conduits 64 include axially-extending portions that extend along the length of plastic drug chamber 58. These portions are shown in section in FIG. 6C. As shown best in FIGS. 2 and 3, bypass conduits 64 also include generally radially-extending portions, which follow the narrowing of the plastic drug chamber. As shown in FIG. 6C, the portions of the inward facing nozzle wall extending between bypass conduits 64 actually support drug plug 62 from the sides and from the front (see also FIGS. 4, 5 and 7). The drug bypass conduits 64 are provided to permit liquid drug disposed in plastic drug chamber 58 to flow from the area between drug plunger 66 and drug plug 62, and around the drug plug, to displace any air in the forward portion of the plastic drug chamber 58, thus priming the apparatus. During actual injection, liquid drug is driven through bypass conduits 64, out injection orifice 54 and into the patient.

Positioned at the proximal end of sleeve 17 is a seal 68 designed to prevent liquid drug from migrating rearwardly along glass cartridge 60 during the priming of apparatus 10 and during injection of drug into the patient. Seal 68 is normally in the form of an O-ring, but other conventional seals may alternatively be used.

A gas piston 70 is positioned along the longitudinal centerline of apparatus 10 in alignment with drug plunger 66 and drug plug 62. Gas piston 70 extends rearwardly or to the left in the figures to contact a gas pressure drive rod 72. Gas piston 70 includes a centrally disposed gas plunger 74 that extends rearwardly into a gas pressure channel 76 that passes through the longitudinal center line of gas pressure drive rod 72. Each of the gas piston 70 and the gas pressure drive rod 72 include cupped portions 78 and 80, respectively, which face each other in a complementing concave configuration.

Gas pressure channel 76 facilitates the passage of gas pressure through the center of the apparatus. A pair of channels 104 extend radially outwardly from gas pressure channel 76 adjacent the rearward end thereof to facilitate the passage of gas pressure from the periphery of the gas pressure drive rod 72 to gas pressure channel 76.

Figure 7:
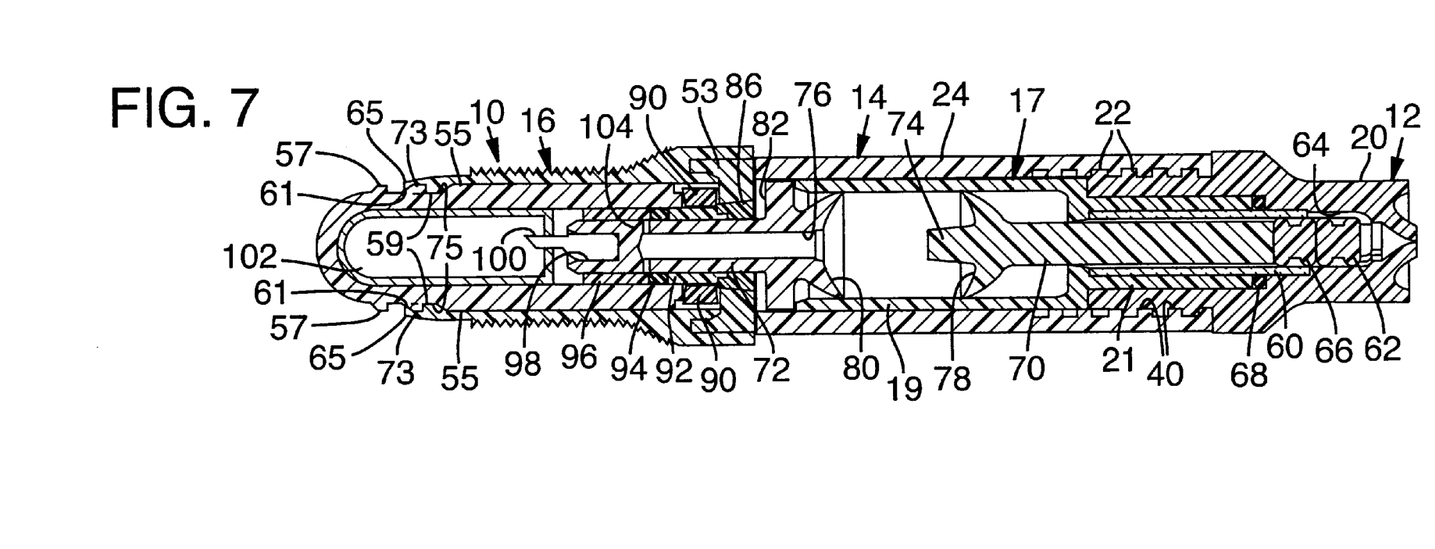
FIG. 7 is a view corresponding to FIG. 5 except that liquid drug has now been injected into the patient, and the apparatus is ready for disposal.

As shown best in FIG. 7, gas piston cupped portion 78 acts to seal gas as it is being expelled out of gas pressure channel 76. The pressurized gas forces the periphery of cupped portion 78 against the inner surface of sleeve 17 to drive gas piston 70 forwardly toward drug plunger 66. The gas pressure is sealed from being exhausted rearwardly by gas pressure drive rod cupped portion 80 that is also forced outwardly against the inner surface of sleeve 17.

Gas pressure drive rod 72 includes a shoulder member 82 that extends radially outwardly almost all of the way to the inner surface of body 24. Shoulder member 82 includes a rearwardly-facing beveled edge 35, which cooperates with chamfered edge 31 of safety tab 30, as will be described in detail below.

Continuing to move rearwardly or to the left in FIGS. 2–5 and 7, body 24 can be seen to include a rearward annulus 84 that engages a fixed washer seat 86 having a beveled or angled left side 86a that in turn holds a trigger ring 88 surrounding gas pressure drive rod 72. A pair of trigger elements 90 are mounted to trigger ring 88, also surrounding gas pressure drive rod 72. As shown best in FIG. 8, a breakaway connection is provided between trigger ring 88 and trigger element 90, for reasons that will be understood as this description continues. Trigger elements 90 are identical to each other, disposed 180° apart. Each trigger element 90 has left and right beveled or angled sides 90a and 90b, respectively. The right beveled sides 90b have a bevel angle that complements that of the left beveled side of fixed washer seat 86a. That angulation is, in the preferred embodiment, approximately 22 degrees.

Continuing along gas pressure drive rod 72, a sliding bushing 92 can be seen. The right hand face 92a of sliding bushing 92 is beveled or angled to correspond to the angulation of the rearward beveled faces 90a of trigger elements 90, again, typically 22 degrees. Like trigger ring 88, sliding bushing 92 fits around gas pressure drive rod 72. This is not a sealing engagement, however, so a sealing ring 94 is positioned immediately rearwardly or to the left of sliding bushing 92, also surrounding gas pressure drive rod 72. Sealing ring 94 is typically in the form of an O-ring, but might alternatively take other forms.

Continuing rearwardly or to the left of sealing ring 94, a spacer bushing 96 can be seen surrounding gas pressure drive rod 72 at the rearward or left-most end thereof. Like sliding bushing 92, spacer bushing 96 surrounds gas pressure drive rod 72, but does not provide a sealing fit, gas sealing being provided solely at sealing ring 94.

This rearward or left-most end of gas pressure drive rod 72 includes an undercut piercing pin receiving seat 98 designed to receive a piercing pin 100. Piercing pin 100 is positioned immediately adjacent a forward or right-facing end of a gas cartridge 102 so that when leftward pressure is exerted on piercing pin 100, gas cartridge 102 is pierced, thereby releasing pressurized Nitrogen or other gas from the cartridge to drive the injection process.

Figure 6A:
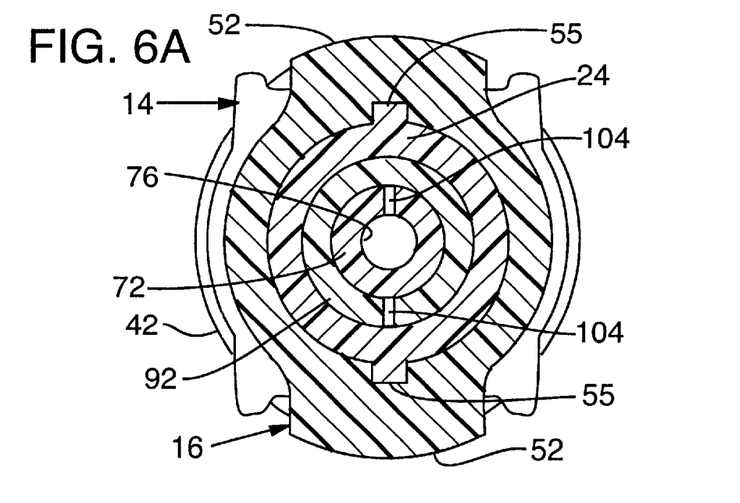
FIG. 6A is an end elevation sectional view taken along line 6A—6A of FIG. 5.
Figure 6B:
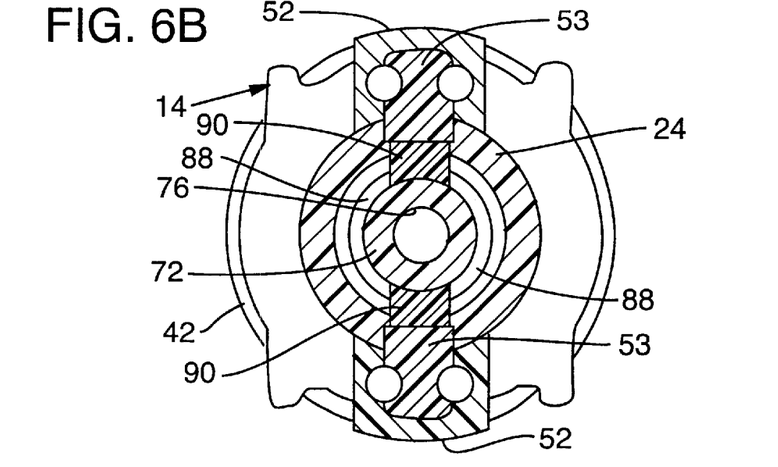
FIG. 6B is an end elevation sectional view taken along line 6B—6B of FIG. 5.
Figure 6C:
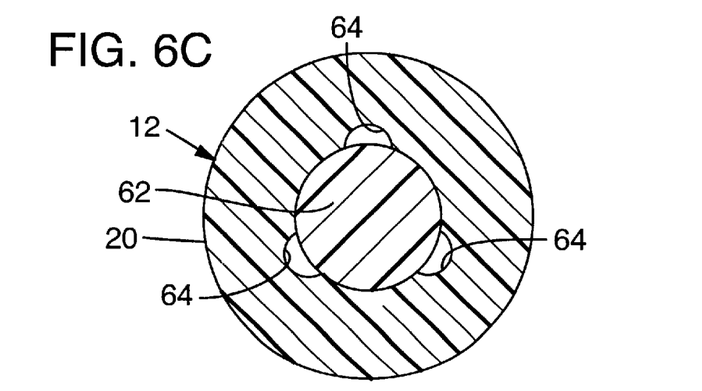
FIG. 6C is an end elevation sectional view taken along line 6C—6C of FIG. 5.

FIGS. 6A, 6B and 6C have been included to show the internal components of apparatus 10 in linear cross section. All of the components depicted in these views have already been discussed, except for the four evenly spaced, generally cylindrical slots that appear in FIG. 6B between trigger members 52 and trigger actuator 53. The slots, which have not been identified with a numeral, are included merely to facilitate automated installation of trigger member 92 into trigger portion 16. They serve no real function in the operation of apparatus 10, which shall now be described.

Operation of the Embodiment of FIGS. 1–11

As mentioned earlier, FIGS. 1–3 depict apparatus 10 in its shipping or storage configuration. When nozzle portion 12 is fully rotated into body portion 14, apparatus 10 is ready for actuation. The conversion process is depicted about half of the way completed in FIG. 4, and completed, ready for injection, in FIG. 5.

It can be seen that during this process of rotating nozzle portion 12 into body 24, gas piston 70 exerts a rightward or distal force on drug plunger 66. As the relative positions of the nozzle and body portions change from the positions of FIG. 3 to those of FIG. 5, drug plunger 66 and drug plug 62 move from being disposed within glass cartridge 60 in storage chamber 51 to positions in which the drug plunger is disposed within the glass cartridge, but the drug plug is in its forward-most position in plastic drug chamber 58, aligned with drug bypass conduits 64. The drug plunger and the drug plug move together until this point because the liquid drug is trapped between them.

Once drug plug 62 clears glass cartridge 60, liquid drug can flow around the drug plunger via drug bypass conduits 64 and dribble out injection orifice 54. This removes any air in the front of the plastic drug chamber 58 and primes apparatus 10 for activation. Prior to actuation, however, gas cartridge 102 must be pierced. This is done by completely threading the nozzle portion 12 into the body portion 14, as depicted in FIG. 5.

However, gas is not yet released to the body portion or the nozzle portion because sealing ring 94 prevents gas from passing beyond that point in the apparatus. Specifically, gas pressure is prevented from flowing into radial channels 104 as long as the sealing ring is disposed rearwardly of the radial channels. Radial channels 104 are also blocked by sliding bushing 92, but because this is not a sealing contact, this does not prevent the passage of gas pressure.

As rotation of nozzle portion 12 into body portion 14 is completed, beveled or chamfered edge 35 of shoulder 82 contacts chamfered edge 31 of safety tab 30. The complementing beveled faces force the safety tab away from the apparatus, breaking the connection at thin webs 33. This disengages the safety tab from the apparatus, permitting it (or "them" if there are two safety tabs) to fall out of trigger engagement slot 28. This clears a space for trigger member (s) 52 to enter the trigger engagement slot(s) 28.

Once rotation of nozzle portion 12 into body portion 14 is complete as depicted in FIG. 5, apparatus 10 is primed and ready for actuation. At this point, gas cartridge 102 has been pierced by piercing pin 100, although the gas pressure is still contained by sealing ring 94. Liquid drug is disposed in plastic drug chamber 58 adjacent injection orifice 54, forward of drug plunger 66 and forward and rearward of drug plug 62. In fact, some of the drug may have actually dribbled out of the drug orifice, simply to ensure that any remaining air has been completely removed from plastic drug chamber 58.

Until the apparatus is actuated, the pair of trigger actuators 53 hold the two trigger elements 90 against gas pressure drive rod 72. A radially-outward force is being exerted on the trigger elements as a result of the forward thrust on sealing ring 94 and the angulation of the interface between sliding bushing 92 and trigger elements 90 at 92a and 90a, respectively, and between fixed washer 86 and trigger elements 90 at 86a and 90b, respectively. The forward thrust is, of course, provided by the gas pressure being exerted on the sealing ring because of the piercing of the gas cartridge.

In order to effect injection, trigger actuation portion 50 is slid to the right or in a forward direction. By sliding trigger actuation portion 50, trigger members 52 are permitted to move into trigger engagement slots 28. Trigger actuators 53 therefore no longer hold trigger elements 90 radially inwardly, and the gas pressure being exerted on sealing ring 94 and sliding bushing 92 causes the sliding bushing to push to the right so that the complementing angled faces cause the trigger elements to be shifted outwardly to the gap formed by the removal of the trigger actuators, as shown in FIG. 7. The radially-outward force on the trigger elements once the trigger actuators have moved is sufficient to break the connection between trigger ring 88 and trigger elements 90 depicted in FIG. 8. Once trigger elements 90 are moved radially outwardly, sliding bushing 92 continues to slide to the right. Along with the sliding of the sliding bushing, sealing ring 94 moves to the right as well, past radial channels 104. This permits gas under pressure to be directed along the interface between spacer bushing 96 and gas pressure drive rod 72, thereby passing into radial channels 104 and gas pressure channel 76. Gas thus rushes through gas pressure channel 76 and gas pressure drive rod 72 and into the interior of body 24. This forces gas plunger 74 out of gas pressure channel 76, exerting gas pressure on gas piston cupped portion 78. This forces the cupped portion against inner sleeve 17, sealing the interface between these components and driving gas piston 70 to the right.

As gas piston 70 is driven to the right, it forces drug plunger 66 forwardly, forcing liquid drug from glass drug storage chamber 51, through drug bypass channels 64, and out through injection orifice 54, into the patient.

The embodiment of FIGS. 1–11 is designed for subcutaneous injection. Therefore it doesn't include an intradermal spacing feature. Such a feature is included in the embodiment depicted in FIG. 12. This variation will now be described.

Figure 12:
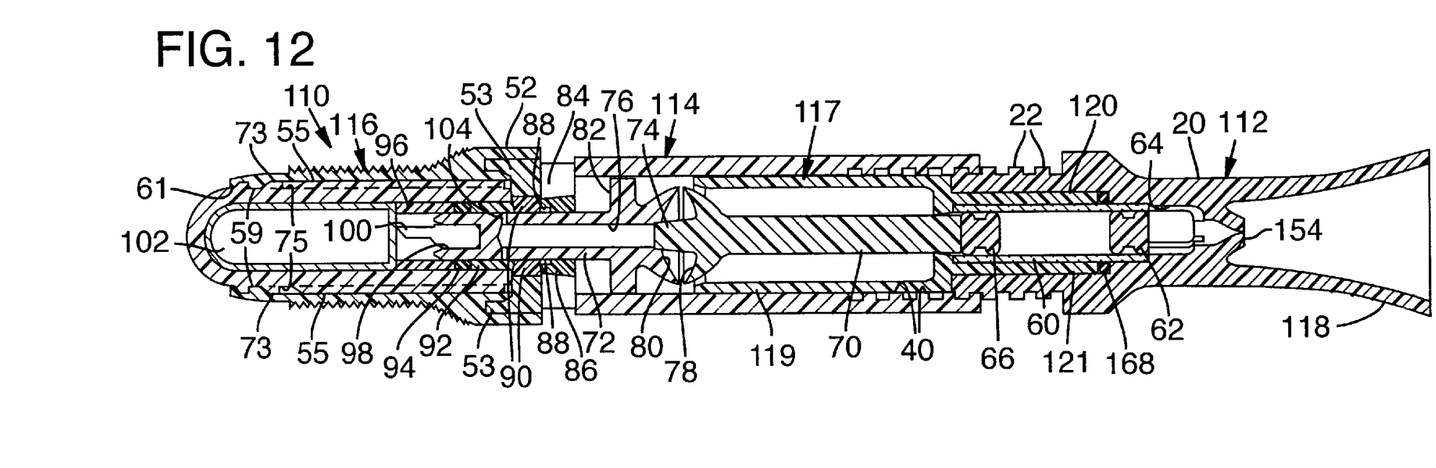
FIG. 12 is a side elevation sectional view of a second embodiment, designed for intradermal injection, showing the unit ready for shipping.

Intradermal Injection Embodiment of FIG. 12

FIG. 12 depicts a second embodiment of the present invention, which is indicated generally at the numeral 110. This embodiment 110 is virtually identical to apparatus 10 except that nozzle portion 112 includes an intradermal spacing section 118. Thus, it can be seen that the injection orifice 154 is spaced away from the skin of the patient during injection. This results in the liquid drug being directed into but normally not entirely through the skin of the patient.

It can be seen in FIG. 12 that, other than dimensional differences and the provision of intradermal spacing section 118, the nozzle portion 112, body portion 114 and trigger portion 116 are essentially identical to corresponding portions of apparatus 10. The size of the injection orifice and the volume of liquid drug are slightly different when comparing apparatus 110 and apparatus 10, but those parameters are up to the product designer and the physicians involved in effecting the injections.

Figure 13:
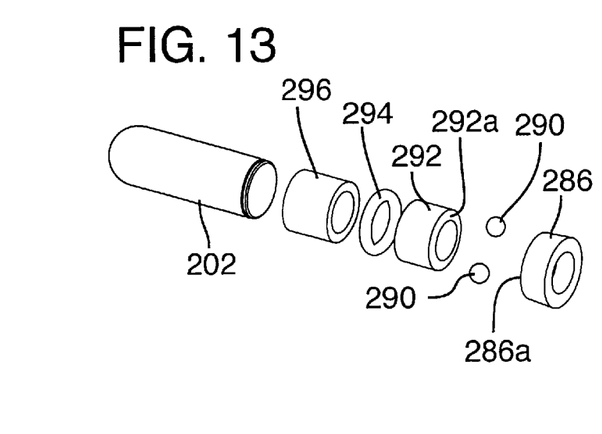
FIG. 13 is a fragmentary, exploded view of a third embodiment, showing ball bearings used in place of the trigger elements.

Embodiment of FIG. 13

FIG. 13 depicts another embodiment that is identical to apparatus 10 of FIGS. 1–11, except that it includes a pair of ball bearings 290 in place of trigger elements 90 and trigger ring 88. Given the spherical configuration of balls 290, they include inclined surfaces (sometimes referred to herein as angled faces) which will cooperate with the complementing inclined surfaces 292a of sliding bushing 292 and 286a of fixed washer 286 in the same fashion as previously described with respect to apparatus 10.

It may be desirable in some applications to include more than two ball bearings; it may also be desirable to include some sort of conventional ball bearing cage (not shown in the figures).

Figure 14:
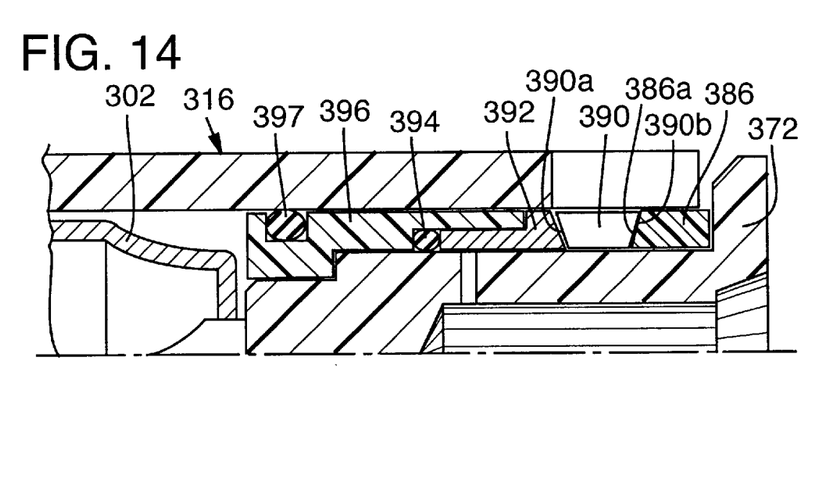
FIG. 14 is a fragmentary, side elevation sectional view of a fourth embodiment, showing the use of a smaller O-ring seal to reduce the amount of axial force on the seal.
Figure 15:
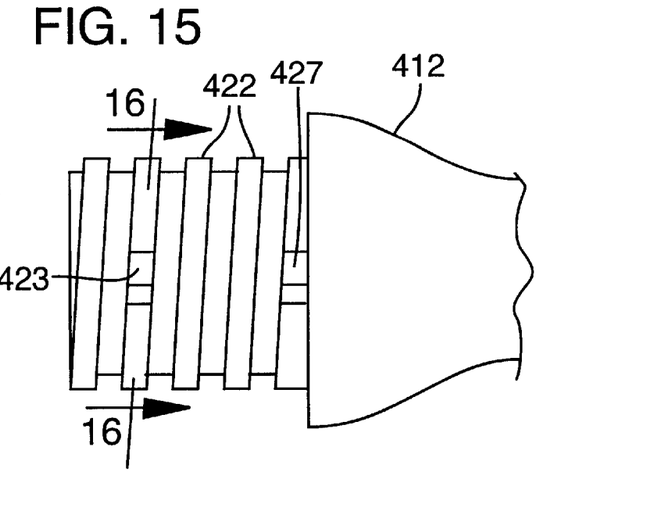
FIG. 15 is a side elevation view of a fifth embodiment, showing only the proximal end of the nozzle portion, the nozzle portion threads including a pair of slots.

Embodiment of FIG. 14

FIG. 14 is a fragmentary sectional view showing an embodiment that includes a smaller O-ring seal than seal ring 94 of apparatus 10 of FIGS. 1–11. This smaller seal, identified at 394, is provided in order to reduce the amount of axial force exerted on the seal ring and the trigger element 390. This embodiment of FIG. 14 is actually the presently preferred mode of practicing the invention.

The embodiment of FIG. 14 is identical in most respects to apparatus 10, except that it includes a spacer bushing 396 that has a pair of steps to accommodate the smaller seal 394. A second seal 397, typically in the form of an O-ring, is included in spacer bushing 396 to prevent pressure from leaking past the interface between body portion 316 and the spacer bushing. Sliding bushing 392 is generally L-shaped to complement the configuration of spacer bushing 396 and the fit of seal 394. A trigger element 390 is shown having angled faces to complement those of sliding bushing 392 and fixed washer 386, as with the prior embodiments. A trigger ring may also be included to facilitate the assembly of trigger elements 390, but it has not been depicted for purposes of simplification.

In operation, after gas cartridge 302 is pierced, forward axial pressure is exerted on seal 394, but because the seal has a smaller surface than seal ring 94, the forward force is less than with apparatus 10. This results in less force on trigger elements 390, which reduces the outward bias on the trigger elements prior to actuation of the unit. The bias is sufficient, however, to break any connection between a trigger ring (not shown) and the trigger elements. In other respects, the construction and operation of this embodiment is identical to that of apparatus 10.

Embodiment of FIGS. 15–18

Figure 16:
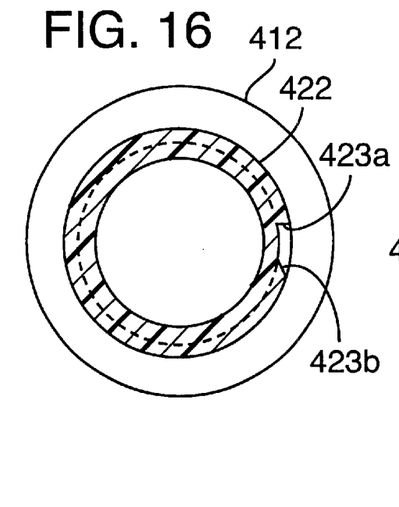
FIG. 16 is an end elevation sectional view taken along line 16—16 of FIG. 15, showing one of the two slots.
Figure 17:
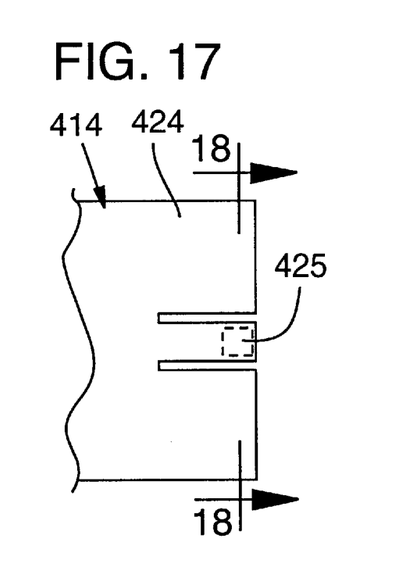
FIG. 17 is a fragmentary side elevation view of the body portion of the fifth embodiment, showing the clip at the distal end thereof.
Figure 18:
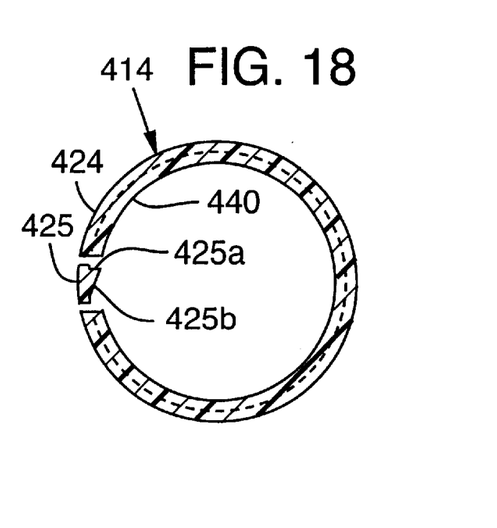
FIG. 18 is an end elevation sectional view taken along line 18—18 of FIG. 17, showing the inclined face of the body portion clip of the fifth embodiment.

FIGS. 15–18 depict another embodiment that includes a variation of the system for engaging nozzle portion 412 and body portion 414. As shown best in FIGS. 15 and 16, a pair of notches 423 and 427 are provided in threads 422 of nozzle portion 412. As shown in FIG. 16, each notch 423 and 427 includes a 90 degree face 423a and an angled face 423b. Complementing these faces, as shown in FIG. 18, is a 90 degree face 425a and an angled face 425b in clip 425. Thus, when nozzle portion 412 is only partially threaded onto body portion 414 for shipping, the natural resiliency of clip 425 enables angled clip face 425b to ride over angled slot face 423b. When threaded beyond that point, 90 degree faces 423a and 425a are in abutment, preventing the nozzle and body portions from threading off of each other. When the nozzle and body portions are entirely threaded onto each other, such as when the gas cartridge has been pierced and the apparatus is ready for actuation, a corresponding 90 degree face of slot 427 engages 90 degree face 425a of clip 425 to prevent the nozzle and body portions from being even partially threaded off each other. This ensures that when the trigger mechanism is actuated, the nozzle and body portions will be fully engaged. It also prevents any disassembly of the unit after the gas cartridge has been pierced. This body and nozzle engagement system of FIGS. 15–18 is presently considered the best mode of engaging the nozzle and body portions.

Other changes and modifications of the present invention can be made without departing from the spirit and scope of the present invention. Such changes and modifications are intended to be covered by the following claims.

I claim:

1. A needle-free injection system comprising:
   a nozzle portion having a glass wall defining a drug storage space, and an injection wall defining a drug injection space, the injection wall being coaxial with the glass wall and defining a plurality of drug bypass conduits disposed adjacent a forward end of the drug injection space;
   a body portion mounted to the nozzle portion such that relative axial movement may be effected between the portions;
   an injection orifice defined at the forward end of the injection space;
   a drug plunger defining a rearward end of the storage space;
   a drug plug initially disposed between the storage space and the injection space, and being displaceable into the injection space adjacent the bypass conduits; and
   a pierceable gas cartridge for providing injection power to the drug plunger.

2. The system of claim 1, further comprising a gas piston extending toward the drug plunger to convey injection power between the gas cartridge and the drug plunger, wherein the nozzle and body portions include complementing threads such that when the portions are threaded into each other, the gas piston exerts a force on the drug plunger.

3. The system of claim 1 wherein the nozzle and body portions include complementing threads, and the threads of at least one of the portions includes a notch with an abutment face and an angled face, the other of the portions including a complementing nib having an abutment face and an angled face to facilitate threaded engagement but to prevent disengagement when the portions are at least partially threaded into each other.

4. The system of claim 3, further comprising a second notch included in the threads of at least one of the portions, the second notch having an abutment face and an angled face, the other of the portions including a complementing nib having an abutment face and an angled face to facilitate threaded engagement but to prevent disengagement when the two portions are substantially fully threaded into each other.

5. The system of claim 1, further comprising an inner sleeve extending between the nozzle and the body portions.

6. The system of claim 5, further comprising a seal disposed at a forward end of the sleeve to prevent drug from migrating rearwardly during the injection process.

7. The system of claim 5 wherein the sleeve includes a larger portion and a smaller portion, the larger portion including an inwardly-facing sleeve wall and wherein the gas piston includes an expanded portion extending to and in sealing relation with the sleeve wall.

8. The system of claim 1, wherein the bypass conduits include axial-extending and radial-extending portions.

9. A needle-free injection system comprising:
   a nozzle portion having a glass wall defining a drug storage space, and an injection wall defining a drug injection space, the injection wall being coaxial with the glass wall and defining a plurality of axially-extending drug bypass conduits that interconnect with a plurality of radially-extending drug bypass conduits;
   an injection orifice defined at a forward end of the injection space;
   a drug plunger defining a rearward end of the storage space;
   a drug plug initially disposed between the storage space and the injection space, and being displaceable into a forward-most position adjacent the bypass conduits; and
   a pierceable gas cartridge for providing injection power to the system.

10. The system of claim 9 further compromising:
    a body portion fitting with respect to the nozzle portion such that effecting relative movement between the body and nozzle portions displaces the drug plunger in a forward direction;
    wherein the drug plunger and the drug plug are initially spaced with respect to each other, disposed within the glass cartridge, and exertion of force on the drug plunger, such as when relative movement is effected between the nozzle and body portions, pushes the drug plunger and drug plug in a forward direction along with any drug disposed therebetween, until the drug plug is disposed in its forward-most position adjacent the bypass conduits.

11. A needle-free injection system comprising:
    a nozzle portion having a glass wall defining a drug storage space, and an injection wall defining a drug injection space, the injection wall being coaxial with the glass wall and defining a plurality of axially-extending drug bypass conduits disposed adjacent a forward end of the injection space;
    an injection orifice defined at the forward end of the injection space;
    a drug plunger defining a rearward end of the storage space;
    a drug plug initially disposed between the storage space and the injection space, and being displaceable into the injection space adjacent the bypass conduits;
    a pierceable gas cartridge for providing injection power to the system;
    a gas piston extending toward the drug plunger to convey injection power between the gas cartridge and the drug plunger;
    wherein the drug plunger and drug plug are initially spaced with respect to each other, disposed within the glass cartridge, and exertion of force on the drug plunger pushes the drug plunger and drug plug in a forward direction along with any drug disposed therebetween, until the drug plug is in a forward-most position, at which time drug flows through the bypass conduits and around the drug plug, thereby displacing any air in the injection space and priming the system.

12. The system of claim 11 wherein the injection wall further defines a plurality of radially extending drug bypass conduits which, in combination with the injection wall, define a forward seat for the drug plug.

13. The system of claim 12, further comprising a gas pressure rod extending coaxially with the glass wall, the gas pressure rod defining an axially extending gas channel and at least one radially extending gas channel.

14. The system of claim 13, further comprising a seal for sealing gas pressure from reaching the gas piston after the gas cartridge has been pierced but prior to actuation of the system.

15. The system of claim 14 wherein the seal is disposed in a channel accessible by gas pressure once the gas cartridge has been pierced, and including at least one spacer member disposed within the channel adjacent the seal, such that when the gas cartridge has been pierced, less force is exerted by the seal than if the seal was larger, and encompassed the entire channel.

16. The system of claim 15 in which the spacer is disposed radially outwardly with respect to the seal.

17. The system of claim 16 wherein the spacer and the channel are annular in configuration.

18. The system of claim 13, further comprising a seal ring disposed around the gas pressure rod slidable between positions rearward and forward of the radial gas channel, the seal ring sealing gas pressure from passing forwardly of the seal ring, such that when the seal ring is disposed forwardly of the radial gas channel, gas pressure can pass through the radial channel and into the axial channel and be directed forwardly to drive the gas piston forwardly.

19. The system of claim 14 wherein the seal is positioned to receive gas pressure when the gas cartridge has been pierced, the gas pressure exerting a forward force on the seal ring, and wherein the system further comprises:
a trigger member disposed forwardly of the seal and having an angled face such that when forward force is exerted on the angled face the trigger member is biased in a first direction; and
a trigger actuator disposed in the first direction with respect to the trigger member to hold the trigger member in place against the bias exerted when the gas cartridge is pierced, so that when the system is actuated and the trigger actuator is moved away from the trigger member, a path is cleared for the trigger member to move in the first direction.

20. The system of claim 19 wherein the trigger member is in the form of at least one ball, and the angled face is a portion of the ball.

21. The system of claim 18 wherein the seal ring is positioned to receive gas pressure when the gas cartridge has been pierced, the gas pressure exerting a forward force on the seal ring, wherein the system further comprises:
a trigger member disposed forwardly of the seal ring, the trigger member including at least one ball positioned such that when forward force is exerted on the ball, the trigger member is biased in a first direction.

22. The system claim 21, further comprising a trigger actuator disposed in the first direction with respect to the trigger member to hold the trigger member in place against the bias exerted when the gas cartridge is pierced, so that when the system is actuated and the trigger actuator is moved away from the trigger member, a path is cleared for the trigger member to move in the first direction.

23. The system of claim 22 wherein the first direction is a radially outward direction.

24. A needle-free injection system comprising:
a nozzle portion having a glass wall defining a drug storage space, and an injection wall defining a drug injection space, the injection wall being coaxial with the glass wall;
an injection orifice defined at a forward end of the injection space;
a drug plunger defining a rearward end of the storage space;
a pierceable gas cartridge for providing injection power to the system;
a gas pressure rod positioned rearwardly of and coaxial with the drug plunger, the gas pressure rod defining an axially extending gas channel and at least one radially extending gas channel;
a seal ring disposed around the gas pressure rod positioned to receive gas pressure when the gas cartridge has been pierced, the gas pressure exerting a forward force on the seal ring, the seal ring being slidable between positions rearward and forward of the radial gas channel, the seal ring sealing gas pressure from passing forwardly of the seal ring, such that when the seal ring is disposed forwardly of the radial gas channel, gas pressure can pass through the radial channel and into the axial channel and be directed forwardly to drive the drug plunger forwardly;
a trigger member disposed forwardly of the seal ring and being positioned and configured such that when forward force is exerted on the angled face, the trigger member is biased radially outwardly;
a trigger actuator disposed radially outwardly of the trigger member to hold the trigger member in place against the outward bias exerted when the gas cartridge is pierced, so that when the system is actuated and the trigger actuator is moved away from the trigger member, a path is cleared for the trigger member to move radially outwardly; and
a sliding member disposed between the seal member and the trigger member and having a forward face in contact with the trigger member, the forward face of the sliding member being angled to complement the trigger member face so that when the gas cartridge is pierced and forward force is exerted on the seal ring, forward force is conveyed to the sliding member, and the angled face of the sliding member and the trigger member cooperate to exert a radially outward force on the trigger member.

25. The system of claim 24 wherein the seal ring is mounted to move forwardly with the sliding member so that when the trigger actuator is moved to facilitate radially outward movement by the trigger member, the seal ring slides forward with the sliding member to a position where the seal ring is forward of the radial gas channel, thereby facilitating a flow of pressure from the gas cartridge through the radial gas channel and into the axial gas channel to drive the drug plunger forwardly, driving drug from the injection space out the injection orifice.

26. The system of claim 24, further comprising another angled face disposed forwardly of the trigger member, and wherein the trigger member includes a second angled face disposed against such other angled face to further facilitate exertion of a radially outward force on the trigger member when forward force is exerted by the sliding member and the seal ring.

27. The system of claim 24 wherein the trigger member includes a beveled face that complements the forward, angled face of the sliding member.

28. The system of claim 24 wherein the trigger member includes at least one ball that contact s and rides on the forward angled face of the sliding member.

29. The system of claim 24, further comprising a body portion positioned rearwardly of and coaxial with the nozzle portion, the nozzle and body portions including threads to threadably engage each other, and wherein an engagement clip is mounted to at least one of the body and nozzle portions to engage the threads of the other portion.

30. A needle-free injection system comprising:
   a nozzle portion defining a forwardly-facing injection orifice;
   a body portion mounted to the nozzle portion, the portions being displaceable toward each other to prepare the system for actuation; and
   a safety tab for preventing actuation prior to the time that relative displacement is effected between the nozzle portion and the body portion, the safety tab being fragibly mounted to one of the body portion or the nozzle portion and including a contact part, the safety tab to be contacted and broken when the portions are displaced toward each other.

31. The system of claim 30 wherein the safety tab contact part includes a chamfered surface that causes the safety tab to be biased away from the portion to which it is mounted when the other portion is displaced toward the safety tab.

32. The system of claim 31, further comprising a shoulder member positioned within one or both of the body and nozzle portions, the shoulder member contacting the safety tab contact part when relative displacement is effected between the portions.

33. The system of claim 32 wherein the shoulder member is chamfered to complement the chamfered surface of the safety tab.

34. The system of claim 30 wherein the portions are gradually displaced toward each other until they are fully engaged, and the safety tab is not broken away until the portions are substantially fully engaged.

35. A method of preparing a needle-free injection unit for injection, the method comprising:
   providing a storage compartment for liquid drug;
   defining an injection orifice forwardly of the storage compartment, through which the liquid drug is selectively injected into the patient;
   providing a pressurized, pierceable gas storage cartridge with a system for conveying pressure to the storage compartment when the cartridge is pierced;
   positioning a seal between the cartridge and the storage compartment to prevent gas pressure from reaching the storage compartment after the cartridge is pierced, but prior to actuation of the unit, the seal being positioned such that the piercing of the cartridge provides axial pressure on the seal;
   providing a trigger having an angled face positioned such that when axial pressure is provided on the trigger, an outward force is exerted on the trigger; and
   positioning a trigger actuator outwardly of the trigger to prevent the trigger from moving outwardly until the unit is actuated.

36. The method of claim 35, wherein the angled face comprises a roller and further comprising providing an outwardly-facing angled face in contact with the roller such that when the unit is actuated, the trigger actuator is displaced and the roller rolls outwardly across the angled face.

37. A method of performing a needle-free injection using a needle-free injection unit, the method comprising:
   providing a storage compartment for liquid drug;
   positioning an injection orifice forwardly of the storage compartment, through which the liquid drug is selectively injected into the patient;
   providing a pressurized, pierceable gas storage cartridge with a system for conveying pressure to the storage compartment when the cartridge is pierced;
   positioning a seal between the cartridge and the storage compartment to prevent gas pressure from reaching the storage compartment prior to actuation of the unit, the seal being positioned such that the piercing of the cartridge provides axial pressure on the seal;
   providing a trigger having a roller positioned such that when axial pressure is provided on the trigger, an outward force is exerted on the trigger;
   positioning a trigger actuator outwardly of the trigger to prevent the trigger from moving outwardly until the unit is actuated, wherein actuation of the unit causes displacement of the trigger actuator, clearing the way for the trigger to move outwardly;
   providing a path of movement for the seal such that when the trigger moves radially outwardly, the seal is free to move in the path of movement;
   providing a pressure path that is clear to provide pressure to the storage compartment once the seal moves in its path of movement, such that providing pressure to the storage compartment forces liquid drug from the storage compartment, through the injection orifice and into the patient;
   piercing the cartridge to prepare the unit for injection; and
   after the cartridge is pierced, positioning the unit against the skin of the patient, and actuating the unit to effect injection.

38. The method of claim 37, further comprising providing an angled face that faces the trigger roller, and wherein when the trigger moves radially outwardly the roller rolls across the angled face.

* * * * *